United States Patent [19]

Sommer

[11] Patent Number: 5,092,675

[45] Date of Patent: Mar. 3, 1992

[54] VACUUM LINE PARTICLE DETECTOR WITH SLAB LASER

[75] Inventor: Holger T. Sommer, Greenbelt, Md.

[73] Assignee: Pacific Scientific Company, Newport Beach, Calif.

[21] Appl. No.: 435,678

[22] Filed: Nov. 14, 1989

[51] Int. Cl.⁵ ............... G01N 21/00; G01V 9/04
[52] U.S. Cl. .................... 356/338; 356/336; 250/222.2
[58] Field of Search ............ 356/388, 332, 339–345, 356/436, 440, 246, 438, 439, 427; 250/576, 574; 377/11

[56] References Cited

U.S. PATENT DOCUMENTS

| | | | |
|---|---|---|---|
| 3,406,289 | 10/1968 | Schleusener | 356/335 |
| 4,380,392 | 4/1983 | Karabegov et al. | 356/336 |
| 4,457,624 | 7/1984 | Goldberg et al. | 356/336 |
| 4,563,763 | 1/1986 | Kuhn | 372/72 |
| 4,571,079 | 2/1986 | Knollenberg | 356/336 |
| 4,637,719 | 1/1987 | Herman | 377/11 |
| 4,685,802 | 8/1987 | Saito et al. | 356/339 |
| 4,746,215 | 5/1988 | Gross | 356/246 |
| 4,798,465 | 1/1989 | Knollenberg | 356/336 |
| 4,842,406 | 6/1989 | VonBargen | 356/338 |
| 4,917,496 | 4/1990 | Sommer | 356/336 |
| 4,984,889 | 1/1991 | Sommer | 356/339 |

OTHER PUBLICATIONS

"The Slab Geometry Laser", William B. Jones, *Laser Focus/Electro-Optics*, pp. 107–114, Sep. 1983.

*Primary Examiner*—Richard A. Rosenberger
*Assistant Examiner*—Hoa Pham
*Attorney, Agent, or Firm*—Lane, Aitken & McCann

[57] ABSTRACT

A particle sensing cell designed to detect the size of particles in a vacuum line for semiconductor processing equipment, a YAG plate is placed adjacent to the vacuum line conduit to define an external laser cavity extending across the conduit between an end face of the YAG plate and a mirror spaced from the end face across the conduit. The YAG plate will generate a laser beam in the shape of a sheet extending across the conduit. A cylindrical lens is positioned adjacent to the mirror to focus light scattered from particles passing through the laser beam on rectilinear photodetector arrays. Pulses generated by the array are applied to pulse amplitude measuring circuitry.

9 Claims, 2 Drawing Sheets

VACUUM LINE PARTICLE DETECTOR WITH SLAB LASER

BACKGROUND OF THE INVENTION

This invention relates to a particle measuring and counting system and, more particularly, to a particle measuring and counting system with an improved particle sensing cell having special applicability for use in a vacuum line and semiconductor processing equipment.

Particle measuring systems have been developed wherein the particles to be measured are entrained in a fluid stream which is passed through a light beam, typically a laser light beam. Particles passing through the beam will scatter light which is collected and focused on a photodetector or photodetectors resulting in electrical pulses being generated. The intensity of the scattered light and, accordingly, the amplitude of the pulses generated by the photo-detectors provide an indication of the particle sizes.

In many systems, it is important to detect every particle in the entrained fluid stream. This need requires that the light beam pass through the entire cross sectional area of the fluid stream entraining the particles. When the fluid stream is a liquid stream, the conduit carrying the stream through the light beam is typically narrowed down to a small cross sectional area so that a high intensity beam can be caused to pass through the entire cross sectional area of the fluid stream. When the fluid stream entraining the particles is a gas stream of substantial density, the gas stream is shaped by a nozzle into the form of the sheet and a laser beam is passed through the sheet-shaped stream along its long dimension as described, for example, in U.S. Pat. No. 4,746,215 to Kenneth P. Gross. However, when the particles are in vacuum, as in semiconductor processing equipment, nozzles cannot readily be used to shape the stream into a sheet-like form. In addition, in order for the vacuum line to efficiently transmit a vacuum to the work area of the semiconductor processing, it is necessary for the vacuum line to have a substantial cross sectional area. Thus, the prior art particle detecting systems involving narrow conduits or nozzles for shaping the fluid stream have limitations which make them not fully satisfactory in detecting particles in a vacuum line such as is employed in semiconductor processing equipment.

SUMMARY OF THE INVENTION

In the system of the present invention, instead of shaping the fluid stream by nozzles or reducing the cross sectional area of the conduit, a slab laser is employed having a YAG plate with a cylindrical mirror on one edge thereof and having an external mirror spaced from the opposite edge thereof to define an external cavity of the laser between the external mirror and the YAG plate. The laser generates a laser beam in the shape of a wide sheet extending across the external cavity. The YAG slab external cavity laser is arranged so that the sheet-like laser beam in the external cavity extends across the vacuum line conduit of the semiconductor processing equipment, so that any particle traveling through the vacuum line conduit will scatter light from the laser beam. A cylindrical lens is located on the wall of the vacuum line adjacent to the laser beam in the external cavity to focus the scattered light from particles passing through the laser beam onto a linear diode array extending along the focal lines of the cylindrical lens. Pulses generated by the diode array are applied to pulse amplitude measuring and counting circuitry. The pulse amplitude measuring and counting circuitry provides a count and measurement of the particles of different sizes passing through the vacuum line. Because the YAG slab laser generates the beam in a broad sheet, the laser beam extends across the relatively large cross sectional area of the vacuum line and particles are detected without the necessity of constricting the vacuum line to a small cross sectional area.

DESCRIPTION OF A PREFERRED EMBODIMENT

Figure 1:
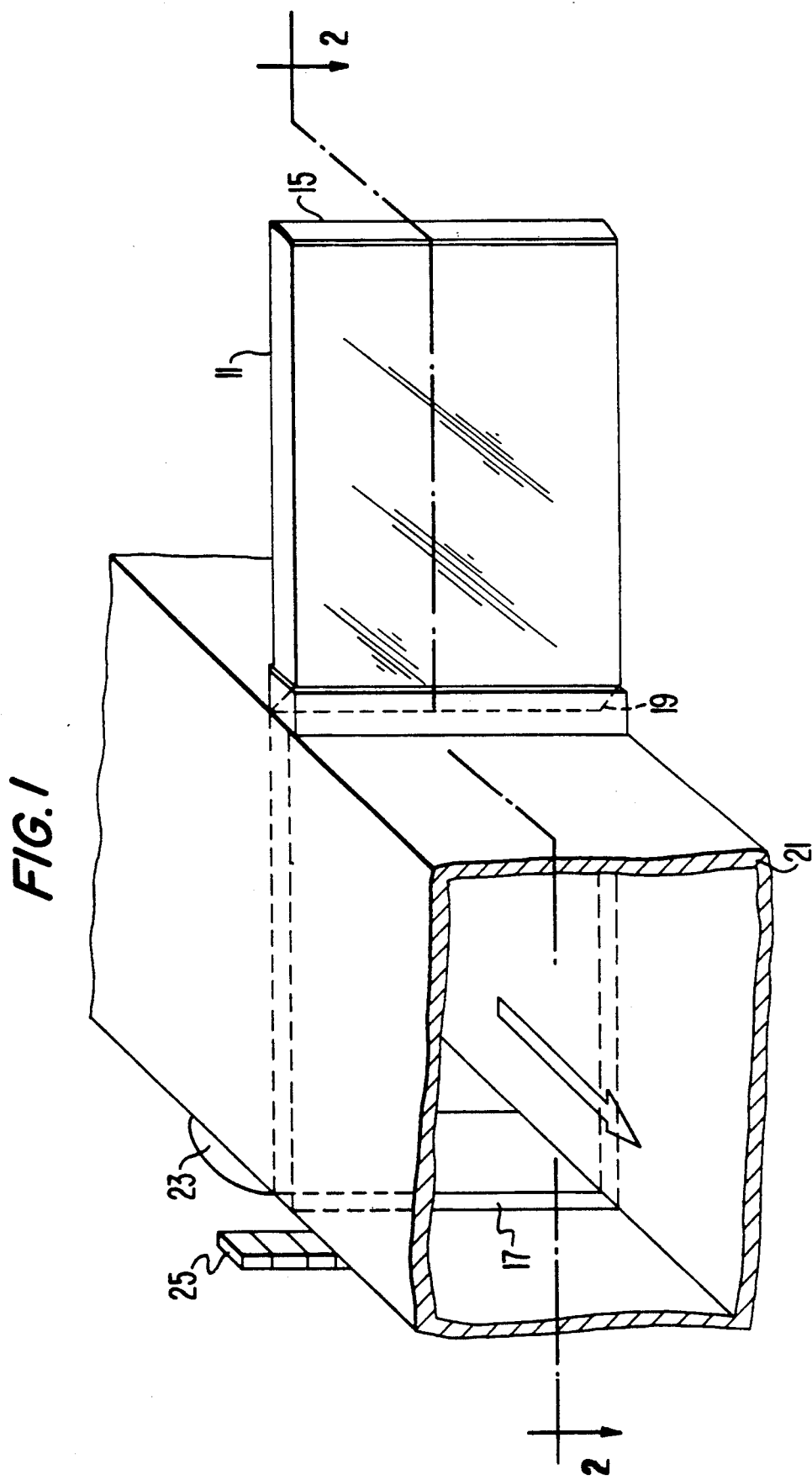
FIG. 1 is a perspective view schematically illustrating a particle sensing cell of the present invention.
Figure 2:
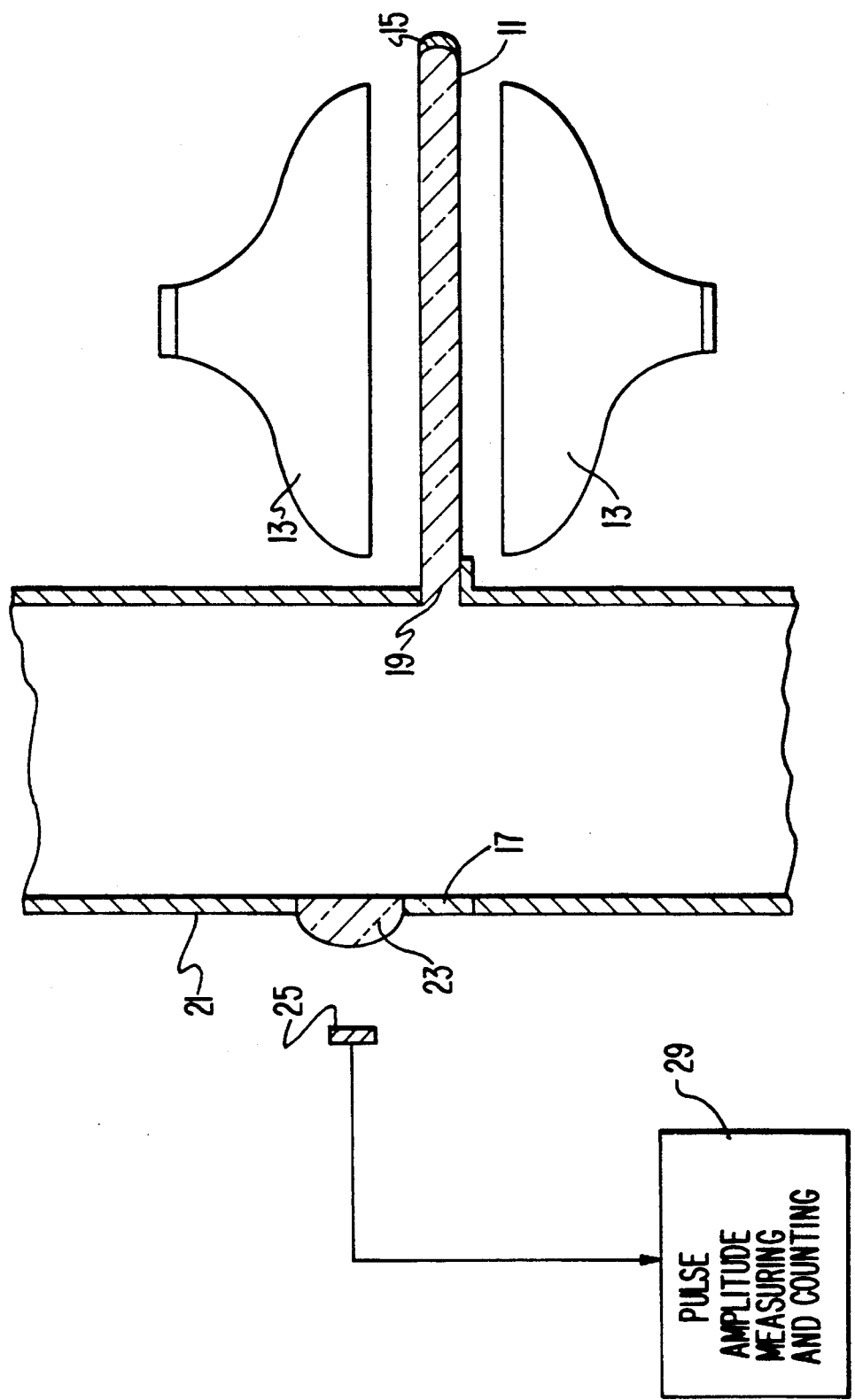
FIG. 2 is a sectional view of the sensor cell shown in FIG. 1 in combination with a block diagram showing the circuitry for responding to the pulses generated by the sensor cell.

As shown in FIGS. 1 and 2, the particle sensing system of the present invention comprises a YAG plate 11 which is a plate of glass laser material. The YAG plate 11 is pumped by white light from lamps 13 located on opposite sides of the YAG plate. Alternatively, the YAG plate may be pumped by laser diode arrays. A curved cylindrical mirror 15 with a 60 cm. curvature radius is formed on one end face of the YAG plate and a flat mirror 17 is spaced from the opposite end face 19 of the YAG plate so as to define an external laser cavity between the mirror 17 and the end face 19 of the YAG plate 11. The end face 19 is beveled as shown in FIG. 2 so that the interface between the glass and a vacuum in the external laser cavity is at the Brewster angle for laser beam passing through the end face 19. When the YAG plate 11 is pumped by white light from the lamps 13 or the laser diode arrays, it will lase and generate a sheet-shaped laser beam extending across the external cavity between the Brewster angle end face 19 of the plate 11 and the mirror 17. The laser beam generated in the external cavity extends across a vacuum line conduit of semiconductor processing equipment so that the sheet-shaped laser beam fills the cross sectional area. The vacuum line conduit has rectangular cross section and the mirror 17 and the Brewster angle end face 19 of the plate 11 extend throughout the height of the vacuum line conduit. The vacuum line conduit is defined by conduit walls 21. Immediately adjacent the flat mirror 17 is a cylindrical lens 23 which also extends throughout the height of the vacuum line conduit as shown in FIG. 1. The lens 23 is shown upstream of the mirror 17, but it also may be positioned downstream of the mirror 17. The lens 23 collects light scattered from particles moving through the sheet-shaped laser beam and focuses the scattered light upon photodetectors of a linear photodetector array 25 extending along the focal line of the cylindrical lens 23. Any particle passing through the sheet-shaped laser beam extending across the vacuum line defined by walls 21 will scatter light to cylindrical lens 23 which will focus this light on one of the photodetectors in the array 25. The photodetector which receives the light will generate an output pulse having an amplitude corresponding to the particle size. The photodetectors in the array are connected in a parallel circuit to have a common output which is applied to a pulse amplitude measuring and counting circuit 29, in which the amplitude of each pulse is measured and the pulses of each different increment of amplitude are counted to provide a count of each particle of each different incremental size passing through the vacuum line defined by the conduit 21. The pulse amplitude measuring and counting circuit 29 may be like that disclosed in U.S. Pat. No. 4,842,406, invented by Kenneth P. VonBargen and assigned to the assignee of this application.

Because the YAG slab external cavity laser generates a laser beam in the form of a wide sheet, complete coverage of the cross sectional area of the vacuum line is obtained.

While the system of the present invention has been described as particularly applicable to vacuum lines and, more particularly, to vacuum lines in semiconductor processing equipment, it will be readily apparent that the system is also applicable to measuring particles in gas streams generally and also in liquid streams.

The above description is of a preferred embodiment of the invention and modification may be made thereto without departing from the spirit and scope of the invention, which is defined in the appended claims.

I claim:

1. A particle sensor comprising a conduit defining a passageway enclosed by a wall, a plate of solid laser material having an end face at the wall of said conduit and facing into the interior of said conduit, means to pump said laser material, a mirror extending parallel to said end face and spaced from said end face across said passageway to define an external laser cavity between said end face and said mirror extending across said passageway, means including said plate and said mirror to generate a laser beam in the shape of a flat sheet extending across said passageway between said mirror and said end face perpendicular to the direction of flow in said passageway, and means to detect light scattered by particles passing through said laser beam.

2. A particle sensor as recited in claim wherein said means to detect light scattered by particles comprises photodetecting means to detect light radiation, a cylindrical lens positioned at the wall of said conduit and arranged to collect light scattered from said laser beam and focus the scattered light onto said photodetecting means.

3. A particle sensor as recited in claim 2, wherein said cylindrical lens is positioned adjacent to said mirror.

4. A particle sensor as recited in claim 3, wherein said lens is elongate in the direction of the axis of the radius of curvature of said lens, said axis extending perpendicularly to the direction of flow through said conduit.

5. A particle sensor as recited in claim 4, wherein said photodetecting means comprises a linear array of photodetectors extending parallel to said axis.

6. A particle sensor as recited in claim 1, wherein said means to generate a laser beam comprises a second mirror formed on an end face of said glass plate opposite to said first mentioned end face.

7. A particle sensor as recited in claim 6, wherein said end faces are parallel rectilinear surfaces.

8. A particle sensor as recited in claim 1, wherein said end face is beveled at the Brewster angle with respect to said laser beam.

9. A particle sensor as recited in claim 1, wherein said conduit comprises a vacuum line conduit with a vacuum being maintained within said passageway.

* * * * *

UNITED STATES PATENT AND TRADEMARK OFFICE
CERTIFICATE OF CORRECTION

PATENT NO. : 5,092,675
DATED : March 3, 1992
INVENTOR(S) : Holger T. Sommer It is certified that error appears in the above-identified patent and that said Letters Patent is hereby corrected as shown below:

<u>IN THE CLAIMS</u>:

Column 4, line 5, after "claim", --1,-- should be inserted.

Signed and Sealed this

Twenty-second Day of June, 1993

Attest:

MICHAEL K. KIRK

*Attesting Officer*   Acting Commissioner of Patents and Trademarks